(12) United States Patent
El Khoury

(10) Patent No.: US 6,465,442 B2
(45) Date of Patent: Oct. 15, 2002

(54) TOPICAL APPLICATION OF MUSCARINIC AND OPIOID AGENTS FOR TREATMENT OF TINNITUS

(76) Inventor: George F. El Khoury, 1561 Ramillo Ave., Long Beach, CA (US) 90815

( * ) Notice: Subject to any disclaimer, the term of this patent is extended or adjusted under 35 U.S.C. 154(b) by 0 days.

(21) Appl. No.: 09/906,057

(22) Filed: Jul. 17, 2001

(65) Prior Publication Data

US 2002/0010191 A1 Jan. 24, 2002

Related U.S. Application Data

(63) Continuation of application No. 09/705,766, filed on Nov. 6, 2000, now Pat. No. 6,262,063, which is a continuation-in-part of application No. 09/318,573, filed on May 27, 1999, now abandoned.

(51) Int. Cl.[7] ................................................ A61K 31/66
(52) U.S. Cl. ........................ 514/78; 514/946; 514/969; 514/940; 514/947
(58) Field of Search .................. 514/969, 487, 514/78, 946, 940, 947

(56) References Cited

U.S. PATENT DOCUMENTS

| | | |
|---|---|---|
| 4,469,702 A | 9/1984 | Schulte |
| 5,064,858 A | 11/1991 | Sapse |
| 5,863,941 A | 1/1999 | Liedtke |
| 6,093,417 A * | 7/2000 | Petrus |

FOREIGN PATENT DOCUMENTS

| | | |
|---|---|---|
| WO | PCT/US94/10771 | 3/1996 |
| WO | WO 97/04762 | 2/1997 |
| WO | WO 98/09623 | 3/1998 |
| WO | WO 98/26770 | 6/1998 |
| WO | WO 00/71518 A2 | 5/2000 |

OTHER PUBLICATIONS

Young II Moon, Recent therapy of tinnitus, J of the Korean Medical Assoc., 1977, vol. 20/7, pp. 598–604.*
Betahistine–induced Vascular Effects in the Rat Cochlea, The American Journal of Otology/vol. 14, No. 1, Jan. 1993.
What You Need to Know—Hearing Loss and Inner Ear Diseases—Can They be Cured? Singapore Medj 1999: vol. 40(1), pp. 60–61.
DECADRON oordruppets met neomycine. S Zintuigen, Gecombineerde Opthalmologicia–Otologica, 1996.
Cervical Trauma Tinnitus, International Tinnitus Journal, vol. 4, No. 1, 31–33, (1998).
Meniere's Disease, Journal AOA, vol. 73, Mar. 1974.
Effects of Droperidol in Management of Vestibular Disorders, 1976.
Burprenorhine Hydrochloride/Butorphanol Tartrate, 1994.

* cited by examiner

*Primary Examiner*—William R. A. Jarvis
*Assistant Examiner*—Vickie Kim

(57) ABSTRACT

The present invention relates to a compositions and methods for treating tinnitus. In preferred embodiments of the invention, muscurinic and/or opioid agents are administered to the affected ear in amount effective to relieve one or more tinnitus symptoms. A preferred agent is an anticholinesterase inhibitor, such as neoostigmine.

4 Claims, No Drawings

TOPICAL APPLICATION OF MUSCARINIC AND OPIOID AGENTS FOR TREATMENT OF TINNITUS

This application is a continuation of 09/705,766 filed Nov. 6, 2000 Pat. No. 6,262,063 which is a continuation-in-part of application Ser. No. 09/318,573, filed May 27, 1999, now abandoned, which is hereby incorporated by reference in its entirety.

BACKGROUND OF THE INVENTION

The present invention relates to compositions and methods for treating tinnitus. Tinnitus can be described as "ringing" and other head noises that are perceived in the absence of any external noise source. It is estimated that 1 out of every 5 people experience some degree of tinnitus.

Tinnitus can be classified into two forms: objective and subjective. Objective tinnitus, the rarer form, consists of head noises audible to other people in addition to the sufferer. The noises are usually caused by vascular anomalies, repetitive muscle contractions, or inner ear structural defects. The sounds are heard by the sufferer and are generally external to the auditory system. This form of tinnitus means that an examiner can hear the sound heard by the sufferer by using a stethoscope. Benign causes, such as noise from TMJ, openings of the eustachian tubes, or repetitive muscle contractions may be the cause of objective tinnitus. The sufferer might hear the pulsatile flow of the carotid artery or the continuous hum of normal venous outflow through the jugular vein when in a quiet setting. It can also be an early sign of increased intra cranial pressure and is often overshadowed by other neurologic abnormalities. The sounds may arise from a turbulent flow through compressed venous structures at the base of the brain.

Subjective tinnitus may occur anywhere in the auditory system and is much less understood, with the causes being many and open to debate. Anything from the ear canal to the brain may be involved. The sounds can range from a metallic ringing, buzzing, blowing, roaring, or sometimes similar to a clanging, popping, or nonrhythmic beating. It can be accompanied by audiometric evidence of deafness which occurs in association with both conductive and sensorineural hearing loss. Other conditions and syndromes which may have tinnitus in conjunction with the condition or syndrome, are otosclerosis, Menier's syndrome, and cochlear or auditory nerve lesions. Hearing loss, hyperacusis, recruitment, FMS, and balance problems may or may not be present in conjunction with tinnitus.

Many sufferers report that their tinnitus sounds like the high-pitched background emitted by some computer monitors or television sets. Others report noises like hissing steam, running water, chirping crickets, bells, breaking glass, or even chainsaws. Some report that their tinnitus temporarily spikes in volume with sudden head motions during aerobic exercise, or with each footfall while jogging. Objective tinnitus sufferers may hear a rhythmic rushing noise caused by their own pulse. This form is known as pulsatile tinnitus.

The cause of tinnitus is largely unknown. Various conditions have been identified which are associated with it, including, allergy, diseases, such as Lyme disease, growths/tumors, general health impairments, injuries, noise exposure, syndromes, such as temporo-mandibular joint (TMJ) syndrome, and medication side- effects.

The most important treatment for tinnitus is avoidance of exposure to excessive noise, ototoxic agents, and other factors that may cause cochlear damage. Masking the tinnitus with music or through amplification of normal sounds with a hearing aid may also bring some relief. Although intravenous treatment with antiarrhythmic drugs (e.g., lidocaine) suppresses tinnitus in some individuals, evidence suggests no benefit with oral agents that are potentially suitable for long-term symptom relief. In addition, systemic procaine has been suggested. See U.S. Pat. No. 5,064,858. Among the numerous drugs that have been tried, oral antidepressants (e.g., nortriptyline at an initial dosage of 50 mg orally at bedtime) appears to be most efficacious. Thus, there remains a need for compositions and treatments for tinnitus.

DESCRIPTION OF THE INVENTION

The present invention provides compositions and methods for treating tinnitus and related disorders. In a preferred aspects of the invention, muscarinic and opioid agents are administered to patients in need of such therapy. The agents, alone, or in combination, are preferably administered topically in effective amounts, e.g., by administering a topical, otic composition to the ear.

A further aspect of the invention is to provide a pharmaceutical composition for topical use, comprising a muscarinic and/or opioid agent, and optionally biologically-active agents, such as penetration enhancers to enhance their penetration into the ear. A preferred embodiment is an otic drop dispenser comprising a topical, otic composition comprising an effective amount of a muscarinic or opioid agent and a pharmaceutically-acceptable carrier.

The compositions and methods of the present invention provide a useful way of treating, preventing, and diagnosing tinnitus. For instance, a method of the invention relates to treating tinnitus comprising, administering to the ear a topically effective amount of a muscarinic or opioid agent. By the term "treating," it is meant that tinnitus is ameliorated, e.g., by reducing, relieving, decreasing, etc., one or more symptoms experienced by a patient with tinnitus. Symptoms that can be treated, include, e.g., ringing or other head noises, rushing noises, high-pitched squeals, ringing, bells, or any other symptoms, especially auditory, associated with the disorder. See, above for a more complete description. The therapeutic effect can be short-lived, e.g., one to four hours, or it may be longer. The therapeutic effect can be for any duration and level of relief. For example, the ringing in the ears can be temporarily completely relieved, or it may be relieved only by, e.g., 80%, 75%, 50%, 25%, or less. While the agents used herein for treating tinnitus as described as "muscarinic or opioid agent," this is not meant to imply that these agents must accomplish their therapeutic effect by acting upon the muscarinic or opioid systems.

The composition is administered to the ear. This means that the composition is delivered to inside the ear canal, e.g., to the tympanic membrane. Delivery can be effected by any means, including drops or spray, using any effective instrument, such as an otic drop dispenser. The latter comprises a container for holding a composition in accordance with the present invention and a dropper, or other instrument for placing the composition inside the ear canal, e.g., on the tympanic membrane.

In accordance with the present invention, muscarinic agents are utilized to treat tinnitus. Preferred muscarinic agents are receptor agonists, partial agonists, mixed agonists/antagonists, and acetylcholinesterase inhibitors Preferred agonists are, e.g., acetylcholine and synthetic choline esters, and cholinomimetic alkaloids, e.g., pilocarpine, muscarine, and arecoline and their synthetic congeners, Preferred acetylcholinesterase inhibitors are, e.g., donepezil, tacrine (THA), pyrodostigmine, physostigmine, huperzine, carbamates, thiaphysovenine, phenserine, endrophonium, demarcarium, ambenonium, and preferably, neostigmine. As mentioned previously, there is no requirement that any of the above-mentioned agents operate by acting as a muscurinic agent. Thus, for example, neostigmine is useful in accordance with the present invention, irrespective of whether its effective activity is a result of acetylcholinesterase inhibition. Likewise, for any agent mentioned in accordance with the present invention.

Other inhibitors which can be used in accordance with the present invention, include, e.g., those inhibitors described in U.S. Pat. No. 5,378,723, U.S. Pat. No. 5,171,750, U.S. Pat. No. 5,591,864, U.S. Pat. No. 5,455,245, U.S. Pat. No. 886,007 and chapters 7 and 8 of Goodman and Gilman, *The Pharmacological Basis of Therapeutics*, $9^{th}$ ed., McGraw Hill, New York (1996). Pharmaceutically acceptable salts, prodrugs and derivatives of any of the above-mentioned agents can be utilized, as well.

In accordance with the present invention, opioid agents are utilized to treat tinnitus. These agents can act on one or more opiate receptors, such as mu, delta, and kappa, to which morphine, the enkephalins, and the dynorphins, respectively, bind, and subtypes thereof. Any agent which binds to and stimulates one or more opiate receptors can be used in the present invention. Such stimulation can be complete or it can be partial. Assays for opioid activity are routine, e.g., using receptor binding or an animal model, such as inflamed knee joint hyperalgesia, formalin-induced nociception, and the Randall-Selitto test. Preferred opioid agents are opioid receptor agonists and agonist-antagonists.

Preferred agonists, include, but are not limited to, DAMGO, morphine, heroin, hydromorphone, dermorphin, spiradoline, U50,488, dynorphin A, DPDPE, deltorphin, DSLET, oxymorphone, levorphanol, methadone, meperidine, fentanyl, codeine, hydrocodone, oxycodone, propoxyphene, tramadol, etorphine, EKC, meperidine, and pharmaceutically acceptable salts, prodrugs and derivatives. Preferred opioid receptor agonist-antagonists, include, but are not limited to, buprenorphine, butorphanol (e.g., Stadol), pentazocine, and nalbuphine (e.g., Nubaine). See, Goodman and Gilman, ibid, Page 546–548. Suitable opioid agents, including those specifically mentioned above, are also described in Goodman and Gilman, ibid, chapter 23. Preferably excluded is dextromethorphan.

As used herein, "pharmaceutically acceptable salts, prodrugs and derivatives" refers to derivatives of the above-mentioned agents that are modified by, e.g., making acid or base salts thereof, or by modifying functional groups present on the compounds in such a way that the modifications are cleaved, either in routine manipulation or in vivo, to produce a biologically-active compound, optionally having enhanced prioperties, such as improved stability, absorption, etc. Examples include but are not limited to mineral or organic salts of acidic residues such as amines, alkali or organic salts of acidic residues such as carboxylic acids, acetate, formate, sulfate, tartrate and benzoate derivatives, etc.

Any amount of a muscarinic agent or opioid agent which is effective to treat tinnitus can be used. Such amounts can be determined routinely, e.g., for example by administering such agents to patients until a therapeutic effect is observed. A composition in accordance with the present invention can comprise an opioid agent or muscarinic agent alone, or in combination.

The doses of muscarinic and opioid agents used in accordance with the present invention can be much smaller than those doses normally used for central or systemic effects. For example, doses used in accordance with the present invention preferably range from about $\frac{1}{1000}$th of the IV dose to about $\frac{1}{10}$th of the IV dose. More preferably, doses range from about $\frac{1}{500}$th of the IV dose to about $\frac{1}{20}$th of the IV dose. Most preferably, doses administered in accordance with the present invention are about $\frac{1}{100}$th of the IV dose administered to achieve a centrally-mediated effect. For example, neostigmine is normally administered as 0.1 mg/kg IV to achieve the effect of reversing curare muscle relaxation. In accordance with the present invention, a preferred solution of neostigmine would be about 10 $\mu$g/30 ml to about 10,000 $\mu$g/30 ml, preferably about 500 $\mu$g/30 ml, administered to the ear, e.g., in about 1–5 drops. In accordance with the present invention, a preferred solution of morphine would be about 0.2 mg/30 ml to about 20 mg/30 ml, preferably about 2 mg/30 ml, administered to the ear, e.g., in about 1–5 drops. In accordance with the present invention, a preferred solution of stadol would be about 0.1 mg/30 ml to about 10 mg/30 ml, preferably about 1 mg/30 ml, administered to the ear, e.g., in about 1–5 drops.

Regardless of which agent is used in accordance with the present invention, a preferable dose is that which produces a therapeutic effect. Different agents will likely be used in different amounts, and even according to different administration schedules. In accordance with the present invention, an agent may be applied only once daily in a higher dose, or several times daily in a lower dose. Alternatively, it may be determined that a therapeutic effect can be achieved by the administration of a lower dose only once daily. For other patients, a higher dose administered several times daily may be necessary. Many combinations of dose and administration schedule are acceptable within the scope of the present invention. The only requirement is that the dose be delivered in a schedule which produces a therapeutic effect. Of course, the lower limit for administration is that which will produce a therapeutic effect.

Compositions in accordance with the present invention can be administered in various amounts and regimes as desired, and necessary, to achieve a therapeutic effect. For instance, the compositions may be administered once a day, twice a day, three times a day, four times a day, five times a day, or as often as necessary. For example, a 500 $\mu$g/30 ml (16.67 $\mu$g/ml) neostigmine solution can be administered by drop to the ear every 4–6 hours.

Otic preparations in accordance with the present invention can be used as medicaments in human or veterinary medicine. Suitable vehicles are organic or inorganic substances which are suitable for otic administration, pharmaceutically-acceptable, which do not react with the active compounds, for example water, saline, alchols, vegetable oils, benzyl alcohols, alkylene glycols, polyethylene glycols, glycerol triacetate, gelatin, carbohydrates such as lactose or starch, magnesium stearate, talc and petrolatum. The indicated preparations can be sterilized and/or contain ancillary substances such as lubricants, preservatives, such as thiomersal (e.g., at 50%), stabilizers and/or wetting agents, emulsifiers, salts to influence the osmotic pressure, buffer substances, colorants, and/or aromatizing substances. They can, if required, also contain one or more other active ingredients. The substances of the invention are normally administered analogously to other otically-administered compounds. For example, neostigmine can be administered in an amount to treat tinnitus, preferably in dosages of about 10 $\mu$g/30 ml to about 10,000 $\mu$g/30 ml, preferably about 500 $\mu$g/30 ml, or about 0.5–2 $\mu$g per dosage. By the term "dosage," it is meant the amount of agent administered in a single treatment, e.g., about 0.83 $\mu$g neostigmine administered to the ear in two drops. Morphine can be administered in about 10–15 $\mu$g per dosage; demoral at about 100–150 $\mu$g per dosage; stadol at about 2–4 $\mu$g per dosage. other agents can be administered analogously, taking into account the potency of the drug. However, the particular dose for each individual patient depends on a very wide variety of factors, for example, efficacy of the particular compound used, age, body weight, general state of health, sex, diet, time and route of administration, rate of excretion, drug combination and severity of the particular disease for which the therapy is intended.

In addition to a muscarinic or opioid agent, compositions of the present invention can comprise other ingredients which are phamaceutically-acceptable. In preferred embodiments of the present invention, a topical excipient is selected that does not enhance delivery of the agent to the systemic circulation or to the central nervous system when administered to the ear. For example, in general, it is preferred that the topical excipient not have substantial occlusive properties, which enhance percutaneous transmission through the skin or mucosa into the systemic circulation. Such occlusive vehicles include hydrocarbon bases such as white petrolatum (e.g., Vaseline); anhydrous absorption bases such as hydrophilic petrolatum and anhydrous lanolin (e.g., Aquaphor); and water-in-oil emulsion bases such as lanolin and cold cream.

More preferred are vehicles which are substantially nonocclusive, and generally include those which are water-soluble, such as oil-in-water emulsion bases (creams or hydrophilic ointments) and water-soluble bases such as polyethylene glycol-based vehicles and aqueous solutions gelled with various agents such as methylcellulose, hydroxyethyl cellulose, and hydroxypropyl methylcellulose (e.g., K-Y Gel).

Suitable topical excipients and vehicles can be routinely selected for a particular use by those skilled in the art, and especially with reference to one of many standard texts in the art, such as Remington's Pharmaceutical Sciences, Vol. 18, Mack Publishing Co., Easton, Pa. (1990), in particular Chapter 87. For instance, biologically-active agents in accordance with the present invention can be combined with enhancing agents which enhance the penetration of an agent into the skin or epithelial layers, such as the cells which line the ear canal, the tympanic membrane, etc. For example, suitable enhancers include, e.g., lecithin, ethanol, propylene glycol, water, sodium oleate, leucinic acid, oleic acid, capric acid, sodium caprate, lauric acid, sodium laurate, neodecanoic acid, dodecyl-amine, cetryl lactate, myristyl lactate, lauryl lactate, methyl laurate, phenyl ethanol, hexamethylene lauramide, urea and derivatives, dodecyl N, N-dimethylamino acetate, hydroxyethyl lactamide, phyophatidylcholine, sefsol-318 (a medium chain glyceride), isopropyl myristate, isopropyl palmitate, several surfactants, including poly-oxyethylene (10) lauryl ether (Brij 361 R), diethyleneglycol lauryl ether (PEG-2-L), laurocapram (Azone; 1,1-dodecylazacycloheptan-2-one), acetonitrile, 1-decanol, 2-pyrrolidone, N-methylpyrrolidone, N-ethyl-1-pyrrolidone, 1-methyl-2-pyrrolidone, 1-lauryl-2-pyrrolidone, sucrose monooleate, dimethylsulfoxide (DMSO) about 80% concentration required, decylmethylsulfoxide (n) enhances primarily polar or ionic molecules (soluble in ethanol), acetone, polyethylene glycol 100–400 MW, dimethylacetamide, dimethylforamide, dimethylisosorbide, sodium bicarbonate, various $N_{7-16}$-alkanes, mentane, menthone, menthol, terpinene, D-terpinene, dipentene, N-nonalol and limonene.

As mentioned otic compositions in accordance with the present invention can comprise various ingredients, including other biologically-active-agents, such as antibiotics, e.g., neomycin, anti-inflammatory agents, e.g., steroids, cortisone, analgesics, antipyrine, benzocaine, procaine, etc.

EXAMPLES

Example 1

Otic Composition for Treating Tinnitus

| Ingredient | Amount |
| --- | --- |
| propylene glycol | 5 ml |
| thiomersal (50%) | 0.3 ml |
| water or saline or 70% alcohol | 9.7 ml |
| active drug | |
| neostigmine | 0.25 mg |
| morphine | 2 mg |
| butorphanol | 1 mg |

Example 2

A group of ten patients complaining of tinnitus were treated with an otic solution comprising about 500 μg/30 ml of neostigmine. The results are summarized in Table 1. One to two drops of the solution was administered to the affected ear about once every 4–6 hours. The patients reported relief within about 20 minutes after initial administration of the otic composition. All patients reported significant relief of the tinnitus symptoms, ranging from reduction to elimination of high-pitched background noises, bells, chirping, and other auditory sounds.

Without further elaboration, it is believed that one skilled in the art can, using the preceding description, utilize the present invention to its fullest extent. The preferred specific embodiments are, therefore, to be construed as merely illustrative, and not limiting the remainder of the disclosure in any way whatsoever. The entire disclosures of all applications, patents and publications, cited above and below, including U.S. Ser. No. 08/291,614, filed Aug. 17, 1994, now U.S. 5,589,480, U.S. Ser. No. PCT/96/19618, filed Dec. 12, 1996, U.S. Ser. No. 08/874,254, U.S. Ser. No. 09/028,117, filed Jan. 23, 1998, and U.S. Ser. No. 09/083,431, filed May 29, 1998, are hereby incorporated by reference.

| | Gender | Age | Etiology | Drug | Frequency | Results | Side Effects |
| --- | --- | --- | --- | --- | --- | --- | --- |
| Pt. 1 | F | 47 | tinnitus after mastoidectomy | neostigmine 500 μg/30 cc | every 4–6 hrs. | 80% improvement | None |
| 2 | F | 24 | tinnitus after craniotomy | neostigmine 500 μg/30 cc | every 4–6 hrs. | 80% improvement | None |
| 3 | M | 64 | tinnitus of unknown origin | neostigmine 500 ug/30 cc | every 4–6 hrs. | 80% improvement | None |

-continued

|   | Gender | Age | Etiology | Drug | Frequency | Results | Side Effects |
|---|--------|-----|----------|------|-----------|---------|--------------|
| 4 | M | 52 | tinnitus of unknown origin | neostigmine 500 μg/30 cc | every 4–6 hrs. | 70% improvement | None |
| 5 | F | 58 | tinnitus of unknown origin | neostigmine 500 μg/30 cc | every 4–6 hrs. | 90% improvement | None |
| 6 | F | 71 | tinnitus of unknown origin | neostigmine 500 μg/30 cc | every 4–6 hrs. | 80% improvement | None |
| 7 | M | 47 | tinnitus of unknown origin | morphine 2 mg/30 cc | every 4–6 hrs. | 60% improvement | None |
| 8 | F | 58 | tinnitus of unknown origin | stadol 1 mg/30 cc | every 4–6 hrs. | 60% improvement | None |
| 9 | F | 67 | tinnitus of unknown origin | stadol 1 mg/30 cc | every 4–6 hrs. | 80% improvement | None |
| 10 | M | 73 | tinnitus of unknown origin | stadol 1 mg/30 cc | every 4–6 hrs. | 80% improvement | None |

What is claimed is:

1. A method of treating tinnitus comprising: administering topically inside an ear 0.5–2 μg per dosage of a composition consisting essentially of a muscarinic agent without delivery into the systemic circulation or to the central nervous system.

2. A method of claim 1, wherein the muscarinic agent is an agonist.

3. A method of claim 2, wherein the agonist is an acetylcholine esterase inhibitor.

4. A method of treating tinnitus comprising: administering topically inside an ear 0.5–2 μg per dosage of neostigmine, without delivery into the systemic circulation or to the central nervous system.

* * * * *